United States Patent [19]
Smith

[11] Patent Number: 5,138,714
[45] Date of Patent: Aug. 18, 1992

[54] WINDSHEET OPTICAL DEVICE

[76] Inventor: Ronald I. Smith, R.F.D. #1, Box #95, Dolgeville, N.Y. 13329

[21] Appl. No.: 674,523

[22] Filed: Mar. 22, 1991

[51] Int. Cl.$^5$ ............................................. A61F 9/00
[52] U.S. Cl. ............................................. 2/9; 2/437; 2/439; 2/450; 128/206.23; 128/206.24; 128/863
[58] Field of Search ................... 2/9, 10, 11, 12, 427, 2/437, 439, 454, 206, 450; 128/201.24, 206.23, 206.24, 863; 351/116, 121

[56] References Cited

U.S. PATENT DOCUMENTS

| | | | |
|---|---|---|---|
| 947,636 | 1/1910 | Degges | 2/13 |
| 1,843,847 | 2/1932 | Sutton | 2/439 |
| 2,192,092 | 2/1940 | Miller, Jr. | 2/12 |
| 2,342,982 | 2/1944 | Stern et al. | 2/9 |
| 2,426,266 | 8/1947 | Haas | 2/450 |
| 3,226,729 | 1/1966 | Fucci | 2/13 X |
| 3,394,980 | 7/1968 | Dym | 2/450 X |
| 3,678,929 | 7/1972 | Buscher | 2/427 X |
| 4,852,185 | 8/1989 | Olson | 2/9 |
| 4,884,296 | 12/1989 | Nix, Jr. | 2/9 X |
| 4,944,312 | 7/1990 | Smith | 2/9 |
| 4,964,171 | 10/1990 | Landis | 2/9 |
| 4,972,521 | 11/1990 | Lison | 2/9 |

FOREIGN PATENT DOCUMENTS

| | | | |
|---|---|---|---|
| 64796 | 12/1967 | Fed. Rep. of Germany | 128/206.24 |
| 0016014 | 11/1912 | France | 128/863 |
| 579754 | 5/1942 | United Kingdom | 2/450 |

Primary Examiner—Werner H. Schroeder
Assistant Examiner—Jeanette E. Chapman
Attorney, Agent, or Firm—James P. Hanrath; Thomas R. Vigil

[57] ABSTRACT

The windsheet optical device for protective eye and facial wear on the head of a human user comprises a transparent flexible sheet including left, middle, and right integral sections of sufficient length to cover the front and at least part of the sides of a human face. The sheet has a plurality of vertically spaced slots adjacent to the outer edge of each of the left and right sections axially aligned across from each other and a nose notch extending upwardly from the bottom edge of the middle section dimensioned to seat upon the bridge of a human nose. A pair of buttons are provided at opposite ends of a resilient band and are dimensioned for releasable engagement in a pair of the vertically spaced slots. The resilient band has sufficient tension to flex the transparent flexible sheet from a substantially planar first shape when the windsheet optical device is not worn on the head of a user to a second shape wherein the left and right sections of the sheet bend inwardly towards the head of a user to wrap around at least part of the sides of the user's face without interfering with the user's peripheral vision when the windsheet optical device is worn on the head of a user.

4 Claims, 2 Drawing Sheets

WINDSHEET OPTICAL DEVICE

BACKGROUND OF THE INVENTION

1. Field of the Invention

The present invention is related to optical devices serving as protective eye shields or covering and the like and, more particularly, is directed to a windsheet optical device.

2. Description of the related art including information disclosed under 37 CFR Sections 1.97-1.99.

Various foreign solid, liquid, and gaseous materials may present a poisonous, caustic, or toxic danger to the human eye, and accordingly protective eye coverings or shields have been proposed to eliminate or reduce the risk of this danger. Simple eye glasses designed primarily with corrective lenses may provide some protection against foreign materials but are vulnerable if exposure of foreign materials is introduced over the top or around the sides of the frame for the glasses.

Various goggles may provide protection for the immediate area of the eye yet expose the forehead and facial area of a user. Other protective wear for the eye may interfere with the peripheral vision of the user.

Further, certain protective eye wear may fail to provide for an adjustable fitting to accommodate differing facial structures of users.

The windsheet optical device of the present invention is designed to eliminate or minimize such disadvantageous features of prior art protective eye wear.

SUMMARY OF THE INVENTION

According to the present invention, there is provided a windsheet optical device for wear on a human head comprising a transparent flexible sheet including left, middle, and right integral sections of sufficient length to cover the front and at least part of the sides of a human face. The sheet has a plurality of vertically spaced slots adjacent to the outer edges of each of the left and right sections axially aligned across from each other and a notch upwardly extending from the bottom edge of the middle section dimensioned to seat upon the bridge of a human nose. Also, there is provided a pair of buttons at opposite ends of a resilient band dimensioned for releasable engagement in a pair of the vertically spaced slots. The resilient band is of sufficient tension to flex the sheet from a substantially planar first shape when the windsheet optical device is not worn on the head of a user to a second shape wherein the left and right sections of the sheet bend inwardly toward the head of the user to wrap around at least part of the sides of the user's face when the windsheet optical device is worn on the head of a user.

When worn on the head of a user each side of the transparent flexible sheet bends inward to wrap around the sides of a user's face giving eye and facial protection from foreign caustic, toxic or poisonous materials to a greater portion of the user's face than the immediate eye area. The plurality of vertically spaced slots cooperates with a buttoned resilient band to provide for a vertically adjustable fit accommodating differing facial structures of users and to provide air vents. Further, the tension of the resilient band holds the transparent flexible sheet in its position wrapped around the sides of a user's face without interfering with the peripheral vision of the user.

Additional features and advantages of the present invention will become apparent to those skilled in the art from the following description and the accompanying FIG.'S illustrating the preferred embodiment of the invention, the same being the present best mode for carrying out the invention.

DESCRIPTION OF THE PREFERRED EMBODIMENT(S)

Figure 2:
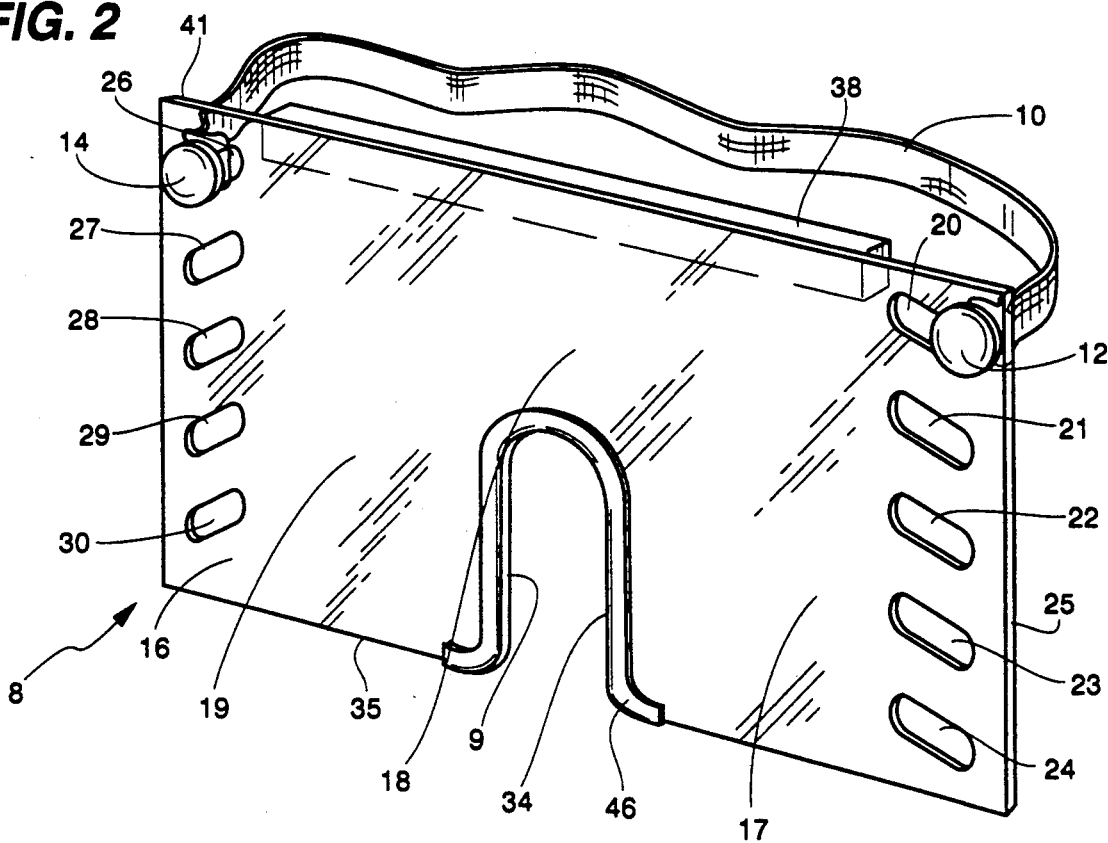
FIG. 2 is a perspective frontal view of the windsheet optical device shown in FIG. 1 but in its collapsed flat state and shows a transparent flexible sheet in a substantially planar shape in buttoned engagement with a resilient band.

Referring now to the drawings, and more particularly to FIG. 2, there is shown therein a perspective frontal view of a preferred embodiment of the windsheet optical device 8 which is bifurcated by a nose slot 9 into two main parts, namely a resilient band 10 with a pair of buttons 12 and 14 tied or otherwise secured to opposite ends of the band 10 and a transparent flexible sheet 16.

The transparent flexible sheet 16 includes left, middle, and right integral sections 17, 18, and 19 respectively (the same being viewed from the perspective of the user wearer) of sufficient length to cover the front and at least part of the sides of a human face. The sheet 16 is made of transparent flexible material and may be fabricated of a suitable flexible transparent thermoplastic synthetic polymer suitable for stamp cutting.

The transparent sheet 16 has a plurality of vertically spaced slots 20, 21, 22, 23 and 24 adjacent to an outer edge 25 of the left section 17 axially aligned across from a plurality of vertically spaced slots 26, 27, 28, 29, and 30 adjacent to an outer edge 31 of the right section 19 thereof. The middle portion 18 has the nose slot 9 which follows an edge 34 extending upwardly from the bottom edge 35 of the middle section 18 of the sheet is dimensioned to seat upon the bridge of a human nose.

Figure 1:
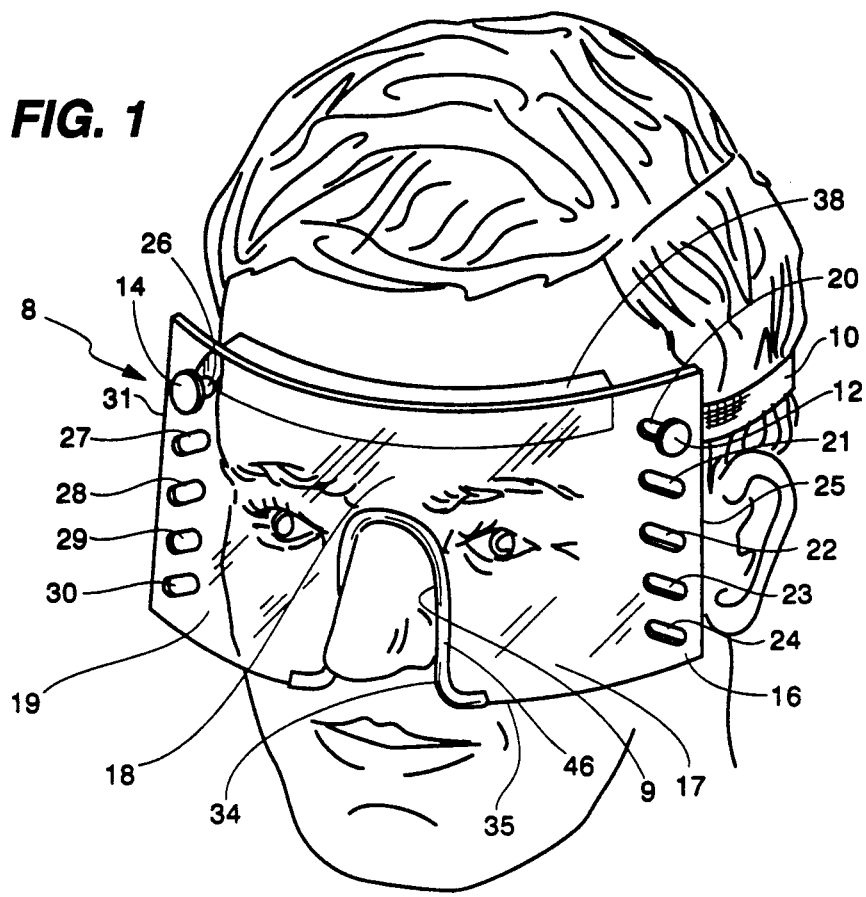
FIG. 1 is a perspective view of the windsheet optical device constructed according to the teachings of the present invention and shows the same worn on the head of a user.
Figure 3:
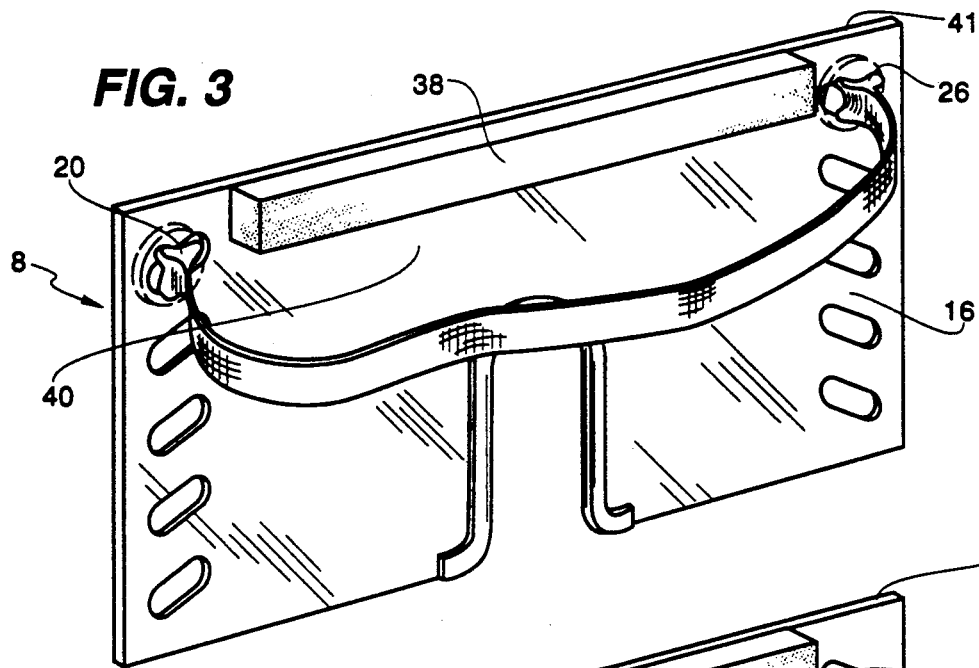
FIG. 3 is a perspective rear view of the windsheet optical device shown in FIG. 2 and shows the transparent flexible sheet in a substantially planar shape in buttoned engagement with the resilient band.

The resilient band 10 has a pair of buttons 12 and 14 at opposite ends thereof dimensioned for releasable engagement in only one pair of vertically spaced slots at a single time, such as slots 20 and 26 respectively as shown in FIG. 1 and in FIG. 3. The plurality of vertically spaced slots 20, 21, 22, 23, and 24 and their cooperative vertically spaced slots 26, 27, 28, 29, and 30 respectively are preferably tilted downwardly toward the outer edges to better capture and retain buttons 12 and 14 at opposite ends of resilient band 10.

Figure 4:
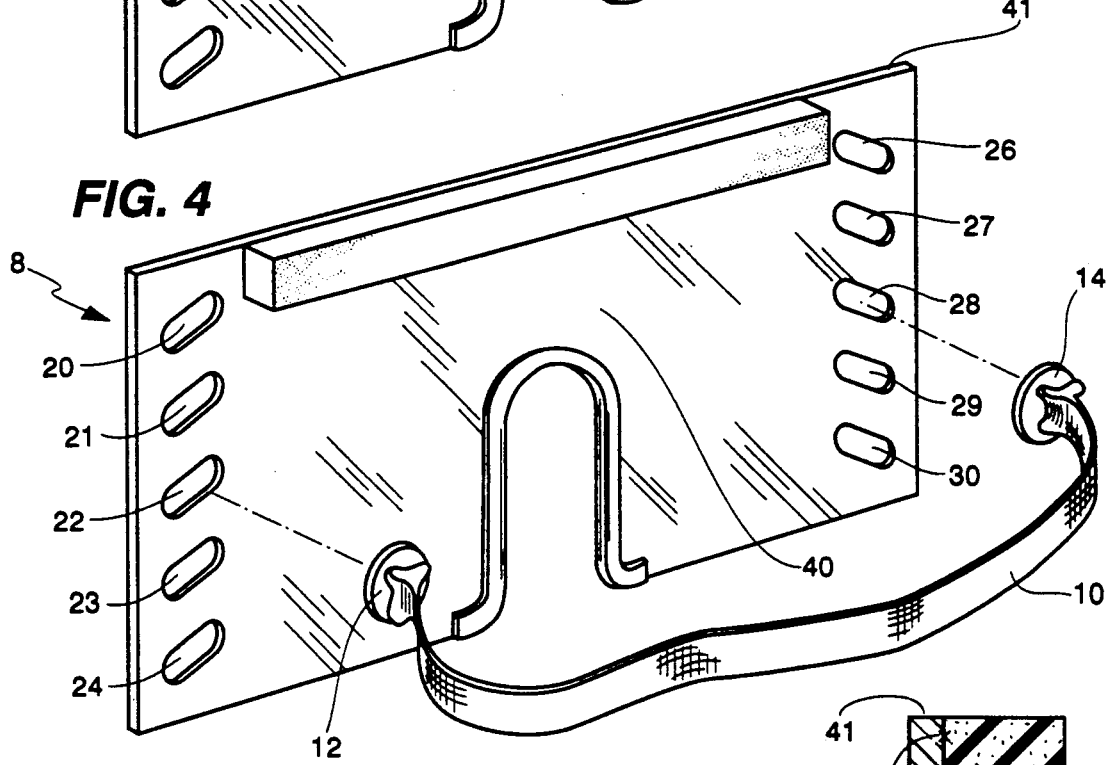
FIG. 4 is a perspective rear view of the windsheet optical device shown in FIG. 3 and shows the buttoned resilient band disengaged from the substantially planar transparent flexible sheet for re-engagement into another pair of the vertically spaced slots such as to provide an adjustable fitting of the windsheet optical device.

As illustrated at FIG. 1, the resilient band 10 is of sufficient tension when engaged with the transparent flexible sheet 16 by buttons 12 and 14 and worn on the head of a user to flex the sheet from the substantially planar first shape illustrated in FIG. 2, FIG. 3, and FIG. 4 to a second shape shown in FIG. 1 wherein the left and right sections 17 and 19 respectively bend inwardly towards the head of the user to wrap around at least part of the sides of the user's face without interfering with the peripheral vision of the user. The substantially planar first shape of the transparent flexible sheet 16 only exists when the windsheet optical device 8 is not worn on the head of a user.

FIG. 3 illustrates a perspective rear view of the preferred embodiment of the windsheet optical device 8. Head cushion 38 is adhered to inner surface 40 immediately below top edge 41 of the flexible transparent sheet 16 to prevent condensation forming an inner surface 40.

FIG. 4 illustrates that a perspective rear view of the preferred embodiment of the windsheet optical device 8, similar to the view in FIG. 3, but shows the resilient band 10 having a pair of buttons 12 and 14 at its opposite ends disengaged from its position as illustrated in FIG. 3 for reinserted engagement with another pair of the vertically spaced slot, such as slots 22 and 28 respectively. Thus the windsheet optical device 8 of the present invention provides for a vertical adjustment of transparent flexible sheet 16 to accommodate different facial structures of users. The slots 21-30 also provide air vents.

Figure 5:
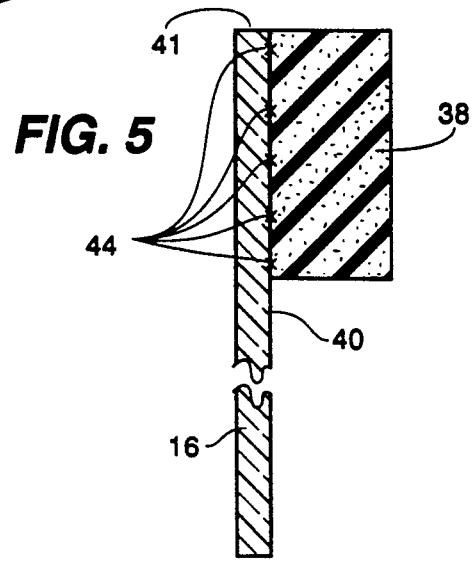
FIG. 5 is a fragmentary side vertical sectional view, is taken along line 5—5 of FIG. 4, and shows a head cushion adhered to an upper back portion of the transparent flexible sheet of the windsheet optical device.

FIG. 5 is a fragmentary side vertical sectional view of the preferred embodiment of the windsheet optical device 8, is taken along line 5—5 of FIG. 4, and shows that the head cushion 38 may be adhered to the inner surface 40 adjacent and below the top edge 41 of the transparent flexible sheet 16 by suitable means 44 for adhering. The means 44 for adhering may comprise double-sided tape or glue.

Figure 6:
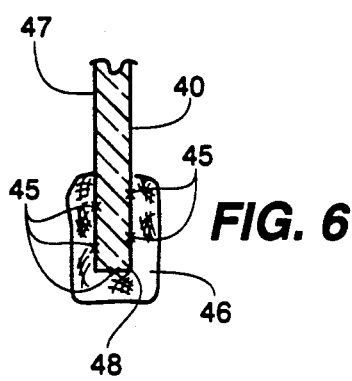
FIG. 6 is a fragmentary side vertical sectional view, is taken along line 6—6 of FIG. 4, and shows a tape stripping adhered around the periphery of the nose notch to the windsheet optical device from a portion of the outer to a portion of the inner surface of the transparent flexible sheet.

FIG. 6 is a fragmentary side vertical sectional view of the preferred embodiment of the windsheet optical device 8, is taken along line 6—6 of FIG. 4 and shows that a stripping 46 may be adhered from a portion of the outer surface 47 over the periphery 48 of the edge 34 of the nose notch 9 to a portion of the inner surface 40 of the transparent flexible sheet 16. The means for adhering the tape strip 45 may be the same as that for the head cushion 38, namely double-sided tape or glue.

It is believed that the windsheet optical device 8 of the present invention in its described embodiment and with its numerous attended advantages will be fully understood from the foregoing description, and that changes may be made in form, construction, and arrangement of the several parts thereof without departing from the scope of the invention, or sacrificing any of the attended advantages. The structure herein disclosed is a preferred embodiment for the purpose of illustrating the invention in order to best explain the principals of the invention and its application and practical use to thereby enable others to utilize the invention. The preferred embodiment illustrated is not intended to be exhaustive or to limit the invention to the precise form disclosed. Accordingly, the scope of the invention is only to be limited as necessitated by the accompanying claims.

I claim:

1. A windsheet optical device for protective eye and facial wear on the head of a human user comprising:
   a transparent flexible sheet including left, middle, and right integral sections of sufficient length to cover the front and at least part of the sides of a human face, said sheet having a plurality of vertically spaced slots adjacent to an outer edge of each of said left and right sections axially aligned across from each other and a nose notch extending upwardly from a bottom edge of said middle section dimensioned to seat upon the bridge of a human nose;
   a resilient band; and
   a pair of buttons at opposite ends of the resilient band dimensioned for releasable engagement in only one pair of said vertically spaced slots at a single time, said resilient band having sufficient tension to flex said sheet from a substantially planar first shape when the windsheet optical device is not worn on the head of a user to a second shape wherein said left and right sections bend inwardly toward the head of the user to wrap around at least part of the sides of the user's face when the windsheet optical device is worn on the head of a user.

2. The windsheet optical device of claim 1 wherein said transparent flexible sheet further includes a head cushion adhered to a top inner surface of said sheet.

3. The windsheet optical device of claim 1 wherein a tape stripping is applied about the periphery of said nose notch.

4. The windsheet optical device of claim 1 wherein the plurality of vertically spaced slots adjacent to the outer edge of each of said left and right sections axially aligned across from each other are angled downwardly toward the outer edges of said sheet.

* * * * *